US005586974A

United States Patent [19]

Martinez et al.

[11] Patent Number: 5,586,974
[45] Date of Patent: Dec. 24, 1996

[54] CONTINUOUSLY ADJUSTABLE HIGH FLOW INSUFFLATOR VALVE

[75] Inventors: Marcus J. Martinez; Anthony S. Tafoya, both of Albuquerque, N.M.

[73] Assignee: Olympus America, Inc., Lake Success, N.Y.

[21] Appl. No.: 428,381

[22] Filed: Apr. 25, 1995

[51] Int. Cl.$^6$ .................................................. A61M 37/00
[52] U.S. Cl. ............................ 604/26; 604/30; 251/314
[58] Field of Search ............................. 604/26; 251/304, 251/314; 137/624.11, 624.13

[56] References Cited

U.S. PATENT DOCUMENTS

| | | |
|---|---|---|
| 2,214,195 | 9/1940 | Frankley . |
| 2,858,847 | 11/1958 | Collins . |
| 4,448,214 | 5/1984 | D'Alessio . |
| 4,501,296 | 2/1985 | Marsoner et al. . |
| 4,705,073 | 11/1987 | Beck . |
| 5,148,946 | 9/1992 | Mizuta et al. . |
| 5,342,294 | 8/1994 | Wiest et al. . |
| 5,346,470 | 9/1994 | Hobbs et al. . |

Primary Examiner—John D. Yasko
Assistant Examiner—Perry E. Van Over
Attorney, Agent, or Firm—Kenyon & Kenyon

[57] ABSTRACT

A valve having a continuously adjustable flow rate which can be used in an insufflator. The valve includes an inlet fluidly coupled with a fluid supply, a chamber fluidly coupled with the inlet, a perforated disk, an outlet, and a two-sided dynamic seal arranged about the perforated disk and having a first side fluidly coupled with the chamber and a second side fluidly coupled with the outlet. By varying a rotational velocity (or frequency) of the perforated disk, the flow rate of the valve can be continuously adjusted.

17 Claims, 12 Drawing Sheets

CONTINUOUSLY ADJUSTABLE HIGH FLOW INSUFFLATOR VALVE

BACKGROUND OF THE INVENTION

The present invention concerns a device for regulating the flow of fluid or gas supplied to, and for regulating pressure within, a cavity. In particular, the present invention concerns an insufflation device for introducing a gas into an intra-abdominal cavity.

Known insufflation devices introduce limited quantities of an insufflation gas, such as carbon dioxide ($CO_2$) for example, into a human body to enlarge a body cavity during certain surgical procedures. However, the amount of $CO_2$ introduced into the body within a certain period of time must be limited because $CO_2$ is absorbed by the blood and increases the carbonic acid present in veineous blood. Some carbonic acid naturally occurs in veineous blood due to work performed by muscles. However, under normal conditions, if too much $CO_2$ per unit time is artificially introduced, the dissolving power of the blood may be exceeded (i.e., gas emboly) leading to the potential for gas bubbles being formed in the coronary vein which endangers the life of the patient.

U.S. Pat. No. 4,207,887 ("the '887 patent") describes a gas insufflation apparatus in which a pressure gauge, which is connected to the body cavity by a measuring duct, closes a solenoid valve when a critical pressure is reached in the body cavity. The valve can be reopened when the intra-cavity pressure falls below a predetermined pressure. Unfortunately, the solenoid valve used in the '887 patent cannot be opened and closed at high frequencies and therefore cannot be used to precisely control the intra-cavity pressure or to control the flow rate of gas to the cavity. Moreover, the intra-abdominal cavity pressure cannot be predicted with an external measuring means.

U.S. Pat. No. 4,048,992 ("the '992 patent") discusses an insufflator having an arrangement for exactly measuring gas pressure and limiting gas flow. Two sensing elements arranged in an expansion cylinder are used to measure the gas pressure. A Verres needle is used to limit the rate of flow. However, the Verres needle cannot limit the pressure. Moreover, the insufflator of the '992 patent requires a series of valves. Finally, the insufflator of the '992 patent cannot predict intra-cavity abdominal pressure.

U.S. Pat. No. 3,885,590 ("the '590 patent") discusses a gas transmission and monitoring device having an adjustable control valve. The adjustable control valve is normally preset to a desired pressure and flow rate and exercises final control over gas delivered to an outlet. However, the device of the '590 patent cannot predict intra-cavity pressure.

U.S. Pat. No. 3,870,072 ("the '072 patent") discusses an insufflator including a shut-off valve which can be closed and which is connected to a drive motor. The drive motor reopens the shut-off valve after a variable regeneration time from the closing of the valve. The device of the '072 patent cannot predict the intra-abdominal cavity pressure and does not permit the pressure or flow rate to be rapidly adjusted.

U.S. Pat. No. 3,901,820 ("the '820 patent") discusses an apparatus for measuring pressure modulated gas in which a wheel or disk repeatedly expands and contracts a bellow via a coupling link. However, the apparatus of the '820 patent is related to infrared analyzers and is not used as an insufflation device or valve.

In view of the above described limitations of the prior art gas valves and insufflation devices, the goal of the present invention is to provide a valve which has a nearly infinitely adjustable displacement volume and which permits an intra-abdominal cavity pressure to be predicted, in real time, without requiring an intra-abdominal measurement.

SUMMARY OF THE INVENTION

The present invention achieves the above mentioned goal by providing a valve including an inlet for receiving fluid flow from a fluid source, a chamber fluidly coupled with the inlet, a chamber outlet fluidly coupled to the chamber, a perforated disk having at least one perforation, a controllable device for rotating the perforated disk an outlet, and a dynamic seal. The dynamic seal has an inlet fluidly coupled with the chamber outlet, and outlet fluidly coupled with the outlet, and is arranged about the perforated disk such that, when the at least one perforation of the perforated disk is aligned with the inlet of the dynamic seal and the outlet of the dynamic seal, the inlet and outlet of the dynamic seal are fluidly coupled.

In a preferred embodiment of the present invention, the inlet can receive fluid flow from a fluid source at a constant pressure.

The chamber may be cylindrical and may accommodate a pressure sensor arranged in the chamber. If the outlet is fluidly coupled with the cavity of a body, a measurement from the pressure sensor is indicative of pressure within the body cavity.

In a preferred embodiment of the present invention, the at least one perforation of the perforated disk includes a plurality of equally spaced perforations at a fixed radial distance from a center of the disk. The plurality of perforations may be round shaped holes or rectangular shaped holes such as squares or slots.

In a preferred embodiment of the present invention, the controllable device is a variable frequency motor which is continuously adjustable.

In a preferred embodiment of the present invention, the perforated disk includes an upstream side and a downstream side and the dynamic seal includes a first part and a second part. The first part includes the inlet of the dynamic seal and an outlet fluidly coupled with the inlet of the dynamic seal and is located adjacent to the upstream side of the perforated disk. The second part includes the outlet of the dynamic seal and an inlet fluidly coupled with the outlet of the dynamic seal and is located adjacent to the downstream side of the perforated disk. The first part and the second part are attached. The first part and the second part are preferably brass. In a preferred embodiment of the present invention, the outlet of the first part includes a concentric step into which is fitted a first top-hat-shaped insert. The first insert contains a fluid pathway fluidly coupled with the outlet of the first part and is biased toward the upstream side of the perforated disk. The inlet of the second part includes a concentric step into which is fitted a second top-hat-shaped insert. The second insert contains a fluid pathway fluidly coupled with the inlet of the second part and is biased toward the downstream side of the perforated disk. The first insert and the second insert are preferably glass.

A first doughnut shaped part is preferably used to bias the first insert towards the upstream side of the perforated disk and a second doughnut shaped part is preferably used to bias the second insert towards the downstream side of the perforated disk. The first doughnut shaped part and the second doughnut shaped part preferably each include a teflon encased spring.

BRIEF DESCRIPTION OF THE DRAWINGS

FIG. 1b is a plan view of the high flow insufflator valve of FIG. 1a.

FIG. 3b is a side view of the perforated disk of FIG. 3a.

DETAILED DESCRIPTION

Figure 1A:
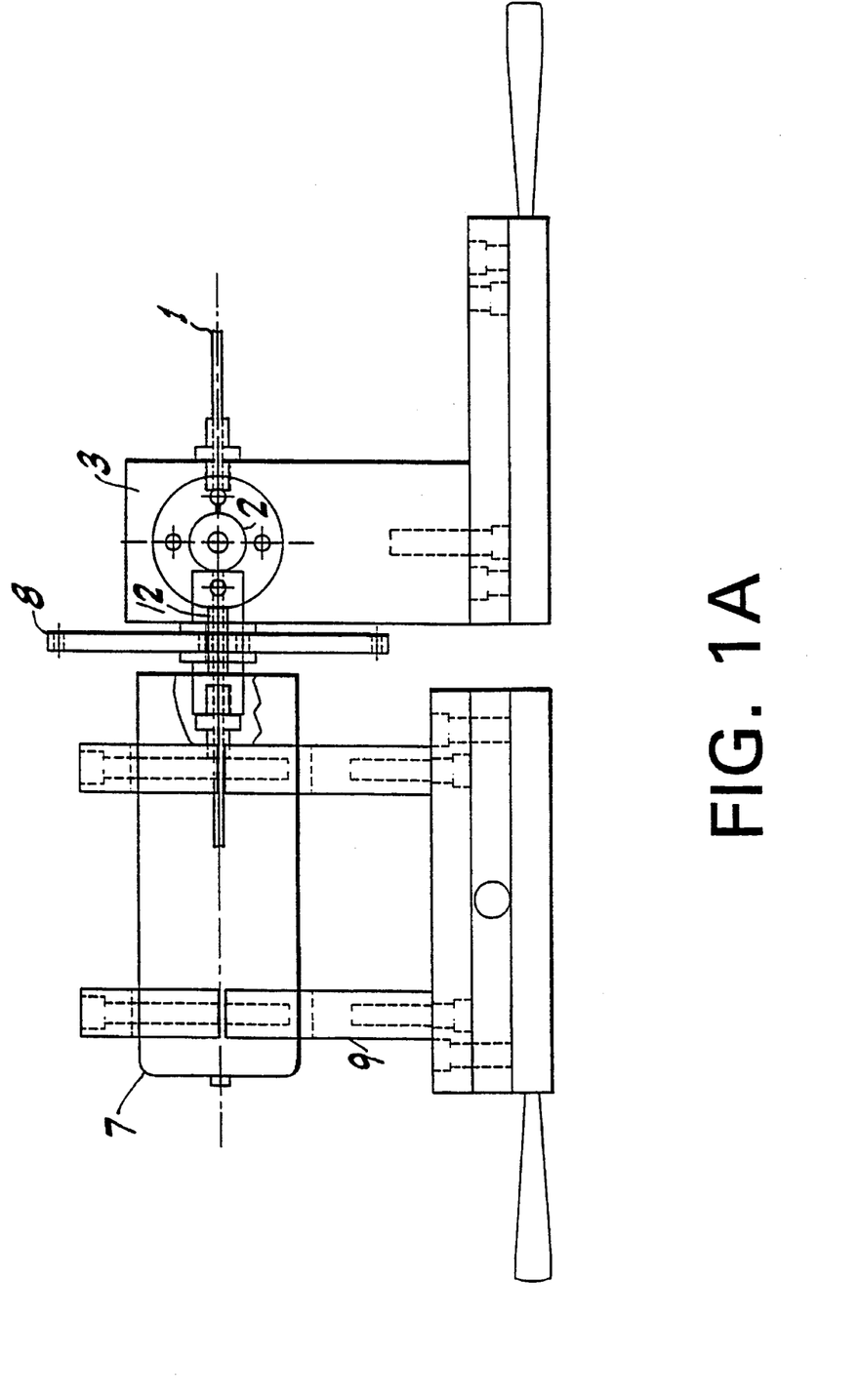
FIG. 1a is a side view of the high flow insufflator valve of the present invention.
Figure 1B:
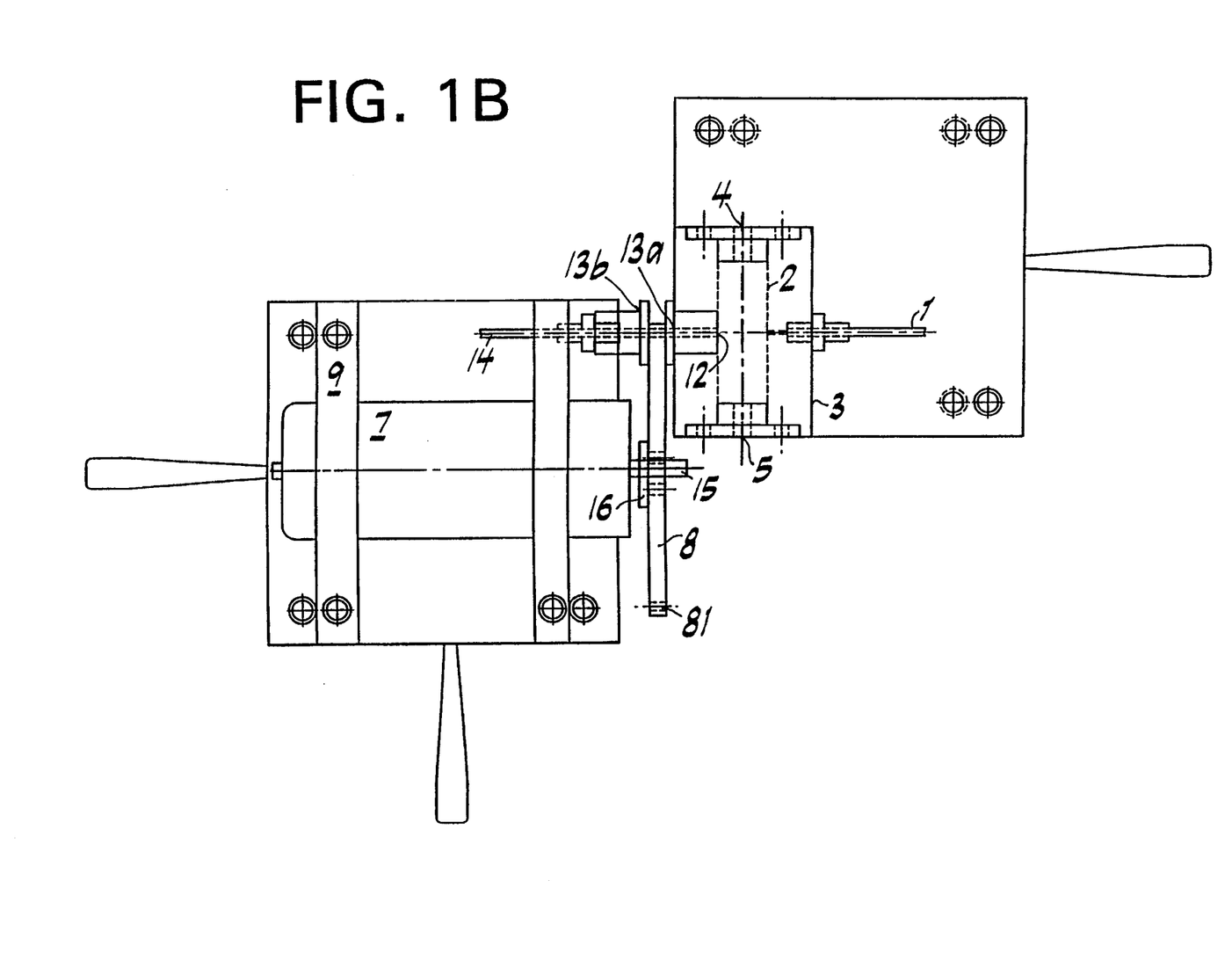

FIGS. 1a and 1b are a side view and a plan view, respectively, of the device of the present invention. The device includes a gas inlet port 1 which is fluidly coupled with a cylindrical chamber 2 formed in a chamber block 3. A reference transducer 4 is arranged within the cylindrical chamber 2. Other transducers, such as a test transducer 5 for example, may also be arranged within the cylindrical chamber 2. The chamber block 3 includes an outlet orifice 12 which is fluidly coupled with the cylindrical chamber 2.

The shape of the cylindrical chamber 2, as well as the locations of the inlet port 1 and the outlet orifice 12, affect the waveform of the pressure within the chamber 2, and thus the waveform of the volume of gas exiting the outlet orifice 12.

Figure 3A:
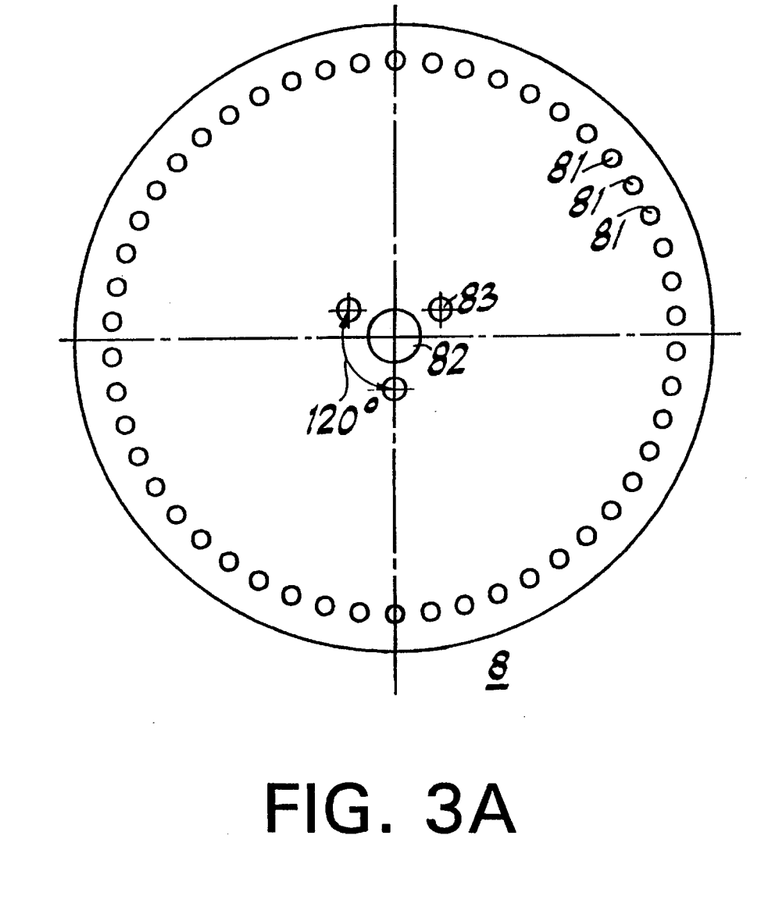
FIG. 3a is an end view of the perforated disk used by the high flow insufflator valve of the present invention.
Figure 3B:
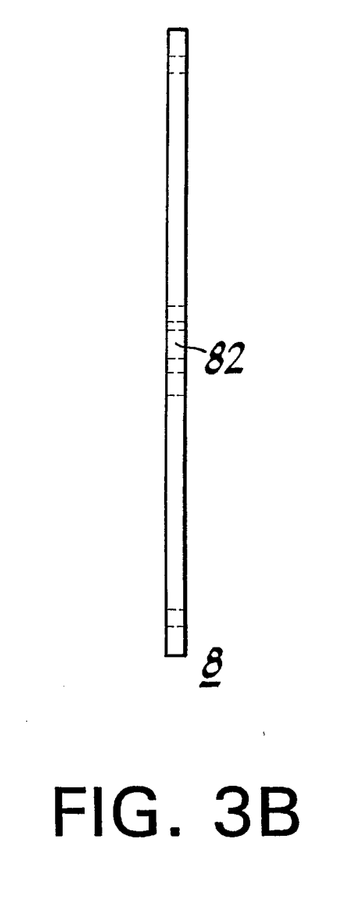
Figure 4A:
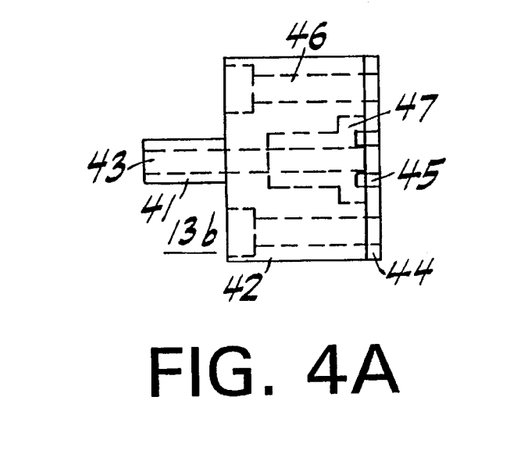
FIG. 4a is a plan view of a first part of a dynamic seal used in the high flow insufflator valve of the present invention.
Figure 4B:
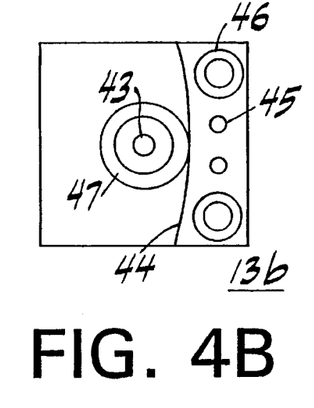
FIG. 4b is an end view of the first part of the dynamic seal.
Figure 4C:
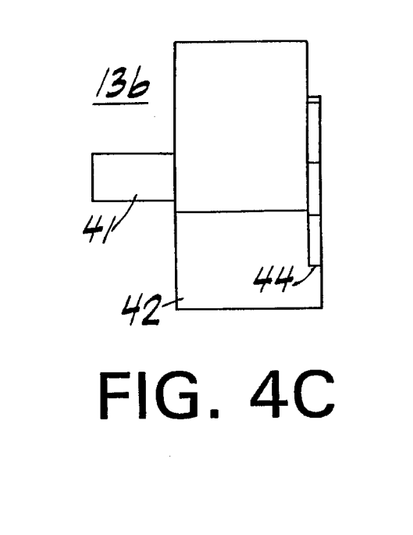
FIG. 4c is a side-plan perspective view of the first part of the dynamic seal.
Figure 4D:
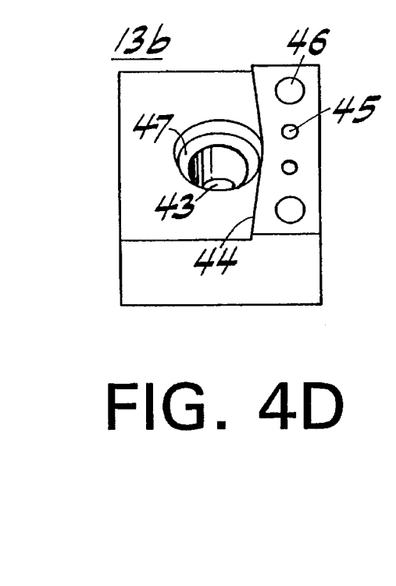
FIG. 4d is an end-side perspective view of the first part of the dynamic seal.
Figure 5A:
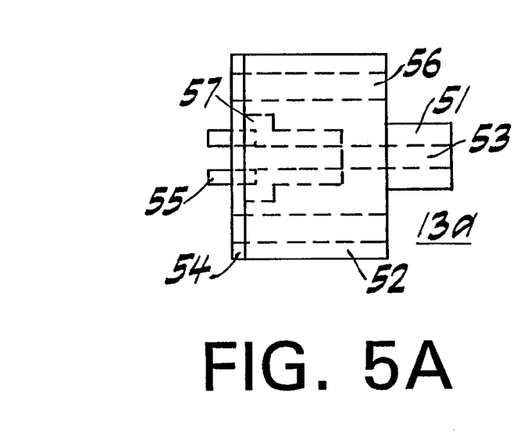
FIG. 5a is a plan view of a second part of the dynamic seal used in the high flow insufflator valve of the present invention.
Figure 5B:
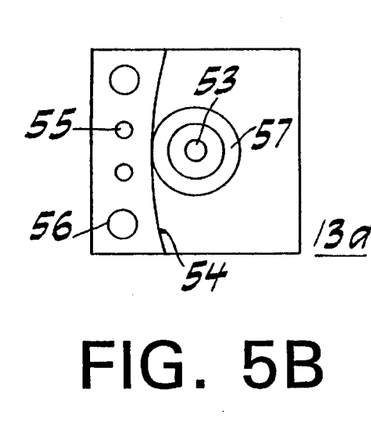
FIG. 5b is an end view of the second part of the dynamic seal.
Figure 5C:
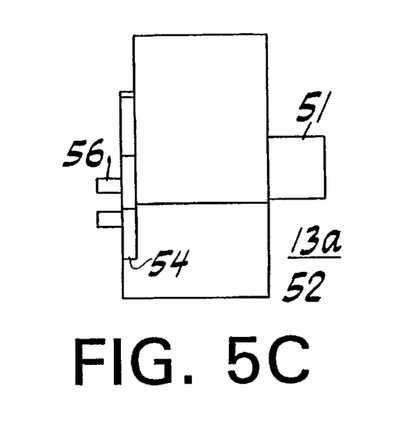
FIG. 5c is a side-plan perspective view of the second part of the dynamic seal.
Figure 5D:
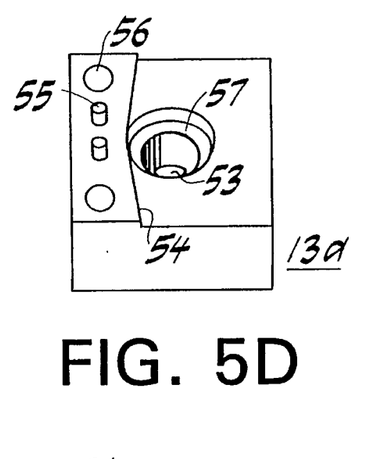
FIG. 5d is an end-side perspective view of the second part of the dynamic seal.

The device of the present invention also includes a DC motor 7 supported by a motor cradle 9. The DC motor 7 includes a shaft 15 having a fixing means 16, such as a collar for example, to which a perforated disk 8 is fixed. As shown in FIG. 3a, the perforated disk 8 includes holes 81 (such as round holes for example) spaced at equal increments at a radial edge region. Alternatively, square holes or slots, for example, can be used rather than round holes. Square holes or slots produce a more sinusoidal pressure waveform. The perforated disk 8 also includes a hole 82 for accepting the shaft 15 of the DC motor 7, and holes 83 for fixing the perforated disk 8 to the shaft collar 16 of the DC motor 7.

As shown in FIG. 1b, a region of the perforated disk 8 is dynamically arranged between a two part dynamic seal 13a–13b. The first part 13a of the two part dynamic seal is fluidly coupled with the outlet orifice 12 of the chamber block 3 and is illustrated in FIGS. 5a through 5d. As shown in FIGS. 5a through 5d, the first part 13a of the two part dynamic seal includes a body 52 having a projection 51, such as a cylindrical projection for example, on a first end and a ledge 54 on an end opposite the first end. The ledge 54 extends from a first side of the body 52 to a second side of the body 52. A least one projection 55, such as a pin for example, extends from the ledge 54. A passage 53 is formed within the projection 51 and the body 52 thereby defining an inlet port at the projection 51 and an outlet port at the body 52. The outlet port is arranged adjacent to the ledge 54 and includes a concentric step 57. Finally, at least one threaded hole 56 is defined in the ledge 54 and the body 52.

The second part 13b of the two part dynamic seal is fluidly coupled with an insufflation line 14 and is illustrated in FIGS. 4a through 4d. The second part 13b of the two part dynamic seal includes a body 42 having a projection 41, such as a cylindrical projection for example, on a first end and a ledge 44 on an end opposite the first end. The ledge 44 extends from a first side of the body 42 to a second side of the body 42. At least one indentation 45, such as a pin hole for example, extends into the ledge 44 and may extend into the body 42. The at least one indentation is shaped so as to mate with the at least one extension 55 of the first part 13a of the two part dynamic seal. A passage 43 is formed within the projection 41 and the body 42 thereby defining an outlet port at the projection 41 and an inlet port at the body 42. The inlet port is arranged adjacent to the ledge 44 and includes a concentric step 47. Finally, at least one hole 46, such as a threaded hole for example, is defined in the ledge 44 and the body 42. The first and second parts 13a and 13b of the two part dynamic seal can be made from brass for example.

Figure 6A:
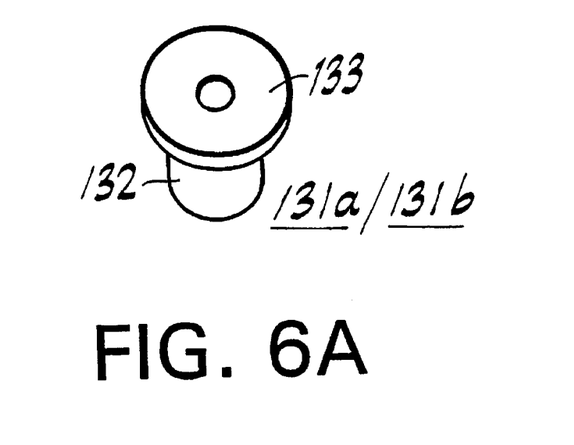
FIG. 6a, is a perspective view of an insert for the dynamic seal.
Figure 6B:
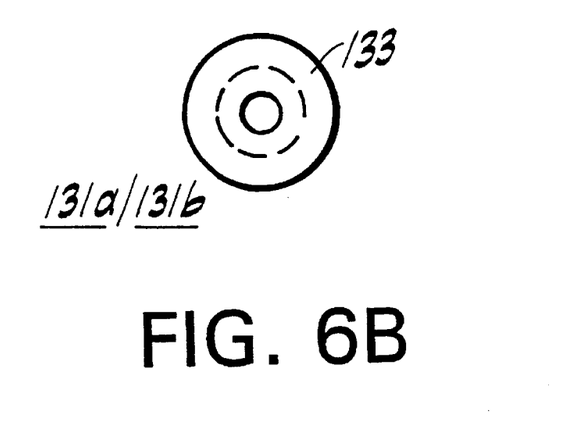
FIG. 6b is a plan view of the insert.
Figure 6C:
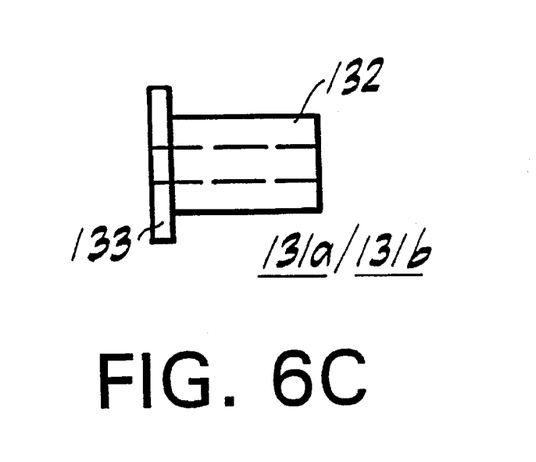
FIG. 6c is an end view of the insert.

FIGS. 6a through 6c illustrate top-hat shaped inserts 131a and 131b, which may be made from machinable glass ceramic for example, which are shaped to fit within the passageways 53 and 43, respectively, of the first and second parts 13a and 13b, respectively, of the two part dynamic seal. The inserts 131a and 131b each include a cylindrical section 132 and a flange section 133. A biasing seal 140, such as a "PARKER POLONPTFE" internal face seal for example, is arranged on the cylindrical section 132, between the flange 133 and the concentric step 47 or 57 of the passage 43 or 53, respectively.

Figure 7:
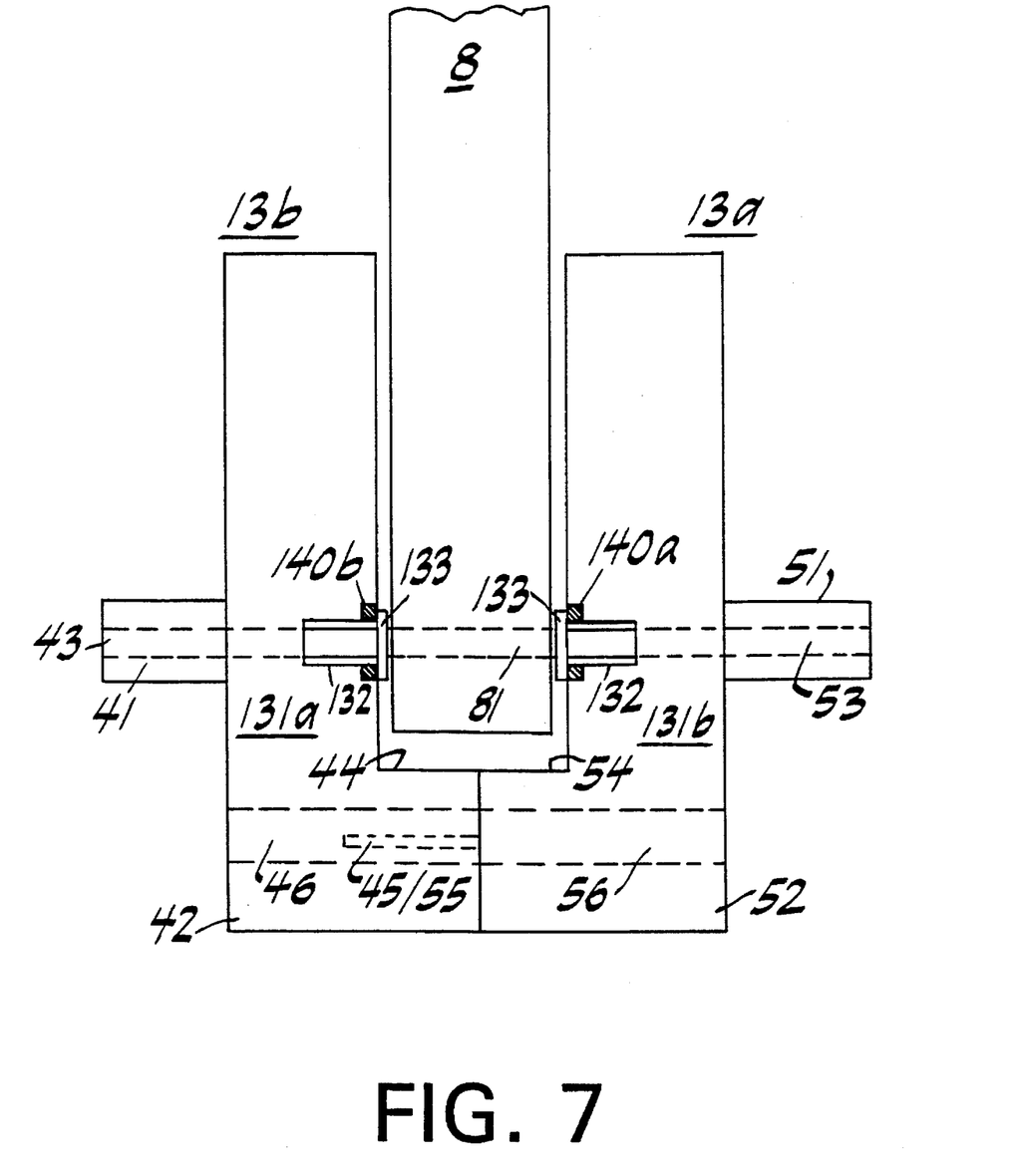
FIG. 7 is a cross-sectional side view of the arrangement of the dynamic seal and the perforated wheel used in the device of the present invention.

As shown in the cross-sectional side view of FIG. 7, the perforated disk 8 is arranged between the inserts 131a and 131b of the first and second parts 13a and 13b of the two part seal such that the holes 81 of the perforated disk can align with the outlet port of the first part 13a of the two part seal and the inlet port of the second part 13b of the two part seal. The biasing seals 140 bias the inserts 131a and 131b towards the surfaces of the perforated disk 8. When the perforated disk 8 rotates at a sufficient angular velocity, an air cushion forms between it and the inserts 131a and 131b. Accordingly, an effective dynamic seal is ensured.

Figure 8A:
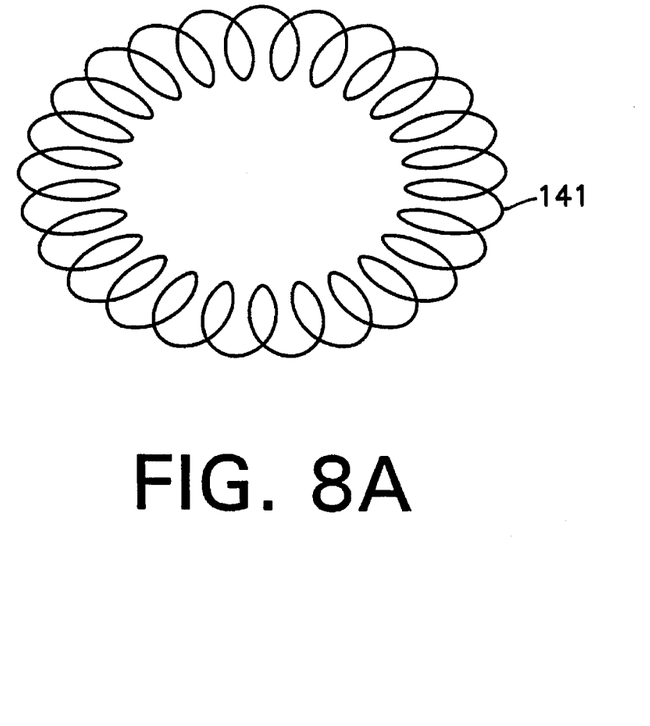
FIG. 8a is a perspective view of a spring used in a biasing seal used in the dynamic seal illustrated in FIG. 7.
Figure 8B:
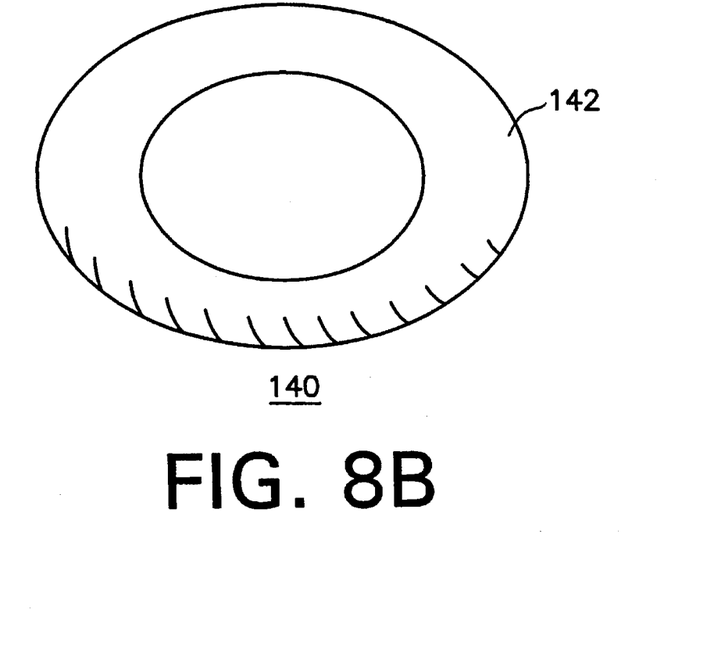
FIG. 8b is a perspective view of the biasing seal.

FIGS. 8a and 8b illustrate the components of the biasing seals 140. FIG. 8a is a perspective view illustrating a spring closed upon itself, i.e., the ends of the spring are attached to form a doughnut-shaped spring 141. The doughnut-shaped spring 141 is coated with Teflon, or enclosed in a Teflon shell 142, to form the biasing seal 140.

Figure 9:
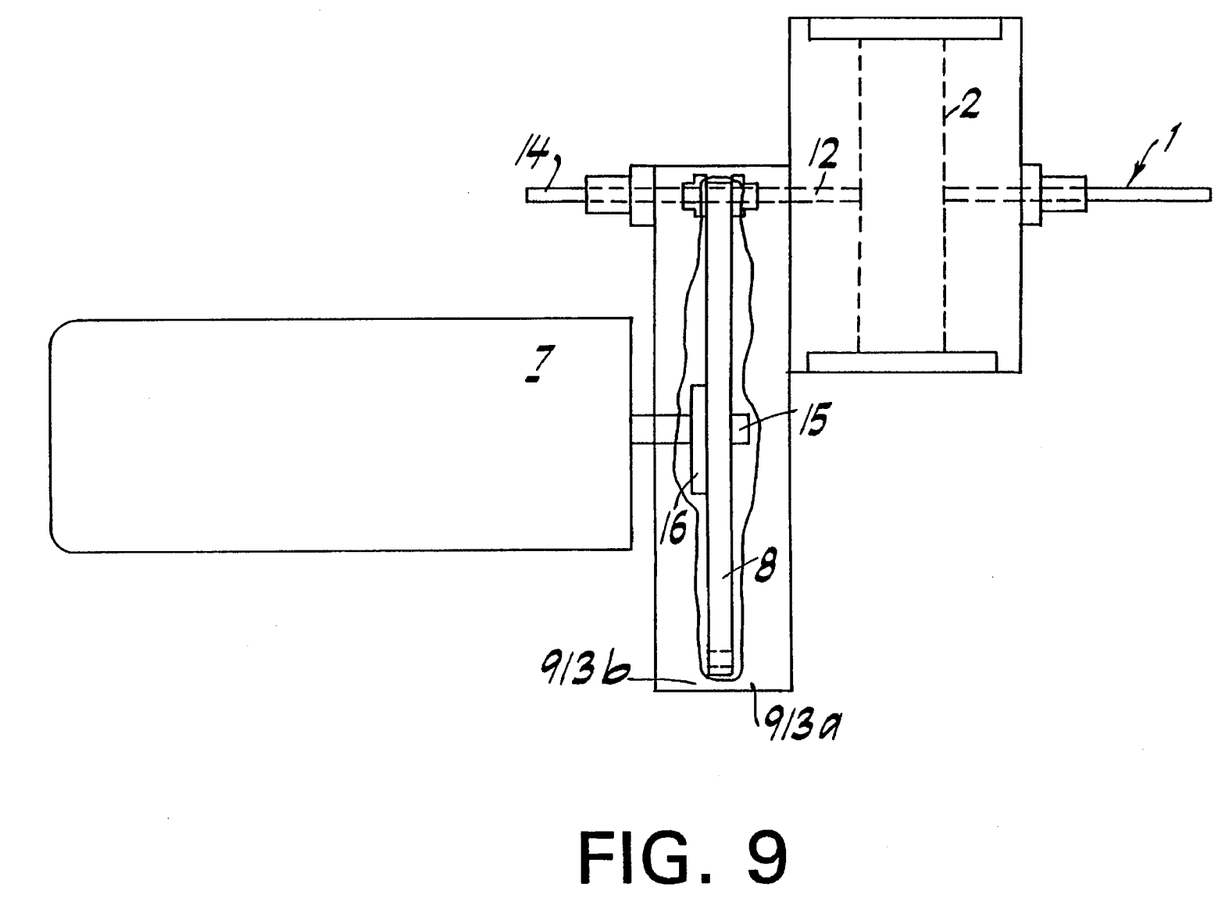
FIG. 9 is a plan view of a second embodiment of the high flow insufflator valve of the present invention which uses an alternative dynamic seal.

Alternatively, as shown in FIG. 9, the two-part dynamic seal 913 can be extended to enclose the entire perforated disk 8. The two-part dynamic seal 913 can be made of similar materials and can have similar attributes as the two-part seal 13. However, this embodiment of the two-part seal 913 surrounds the entire perforated disk 8 and only has an inlet opening (in 913*a*), an outlet opening (in 913*b*), and an opening for the drive shaft (in 913*b*). In a refined embodiment, the disk can be driven by a magnetic coupling, for example, so that a shaft opening in the second part 913*b* of the two-part dynamic seal 913 would not be required.

The device of the present invention operates as follows. Referring to FIGS. 1*a* and 1*b*, gas from an external source is provided (at a constant pressure, for example) to the gas inlet port 1 and from there, fills the cylindrical chamber 2. The reference transducer 4 and/or the test transducer 5 measure the pressure of the gas in the cylindrical chamber 2. Gas exits the cylindrical chamber 2 via the outlet orifice 12.

Referring now to FIG. 7, from the outlet orifice 12, the gas proceeds through the passage 53 in the first part 13*a* of the dynamic seal 13. The gas then proceeds through the insert 131*a* which is biased, by the biasing seal 140, against the perforated disk 8. As is further shown in FIG. 7, when a hole 81 of the perforated disk becomes aligned with the passage through the insert 131*a*, the gas proceeds through the hole 81 and then through a passage in the insert 131*b*, and further proceeds through a passage 43 in the second part 13*b* of the dynamic seal to an insufflation line 14*a*.

The perforated disk 8 is rotated at a controllable angular velocity (or frequency) based on the frequency of the controllable DC motor 7. When a hole 81 of the perforated disk 8 is perfectly aligned with the passages of the inserts 131*a* and 131*b*, the gas flow is a maximum. When a section of the perforated disk without a hole is placed between the passages of the inserts 131*a* and 131*b*, the gas flow is at a minimum. Accordingly, as the perforated disk rotates at a given angular velocity (or frequency), the gas flow oscillates at a corresponding frequency. Pressure values read from the transducers 4 and/or 5 are indicative of the gas flow through the insufflation line 14 and are indicative of a pressure within a cavity to which the insufflation line is fluidly connected. The intra-cavity pressure can be estimated since $V_1 P_1$ (in the cylindrical chamber 2) equals $V_2 P_2$ (in the cavity).

Figure 2A:
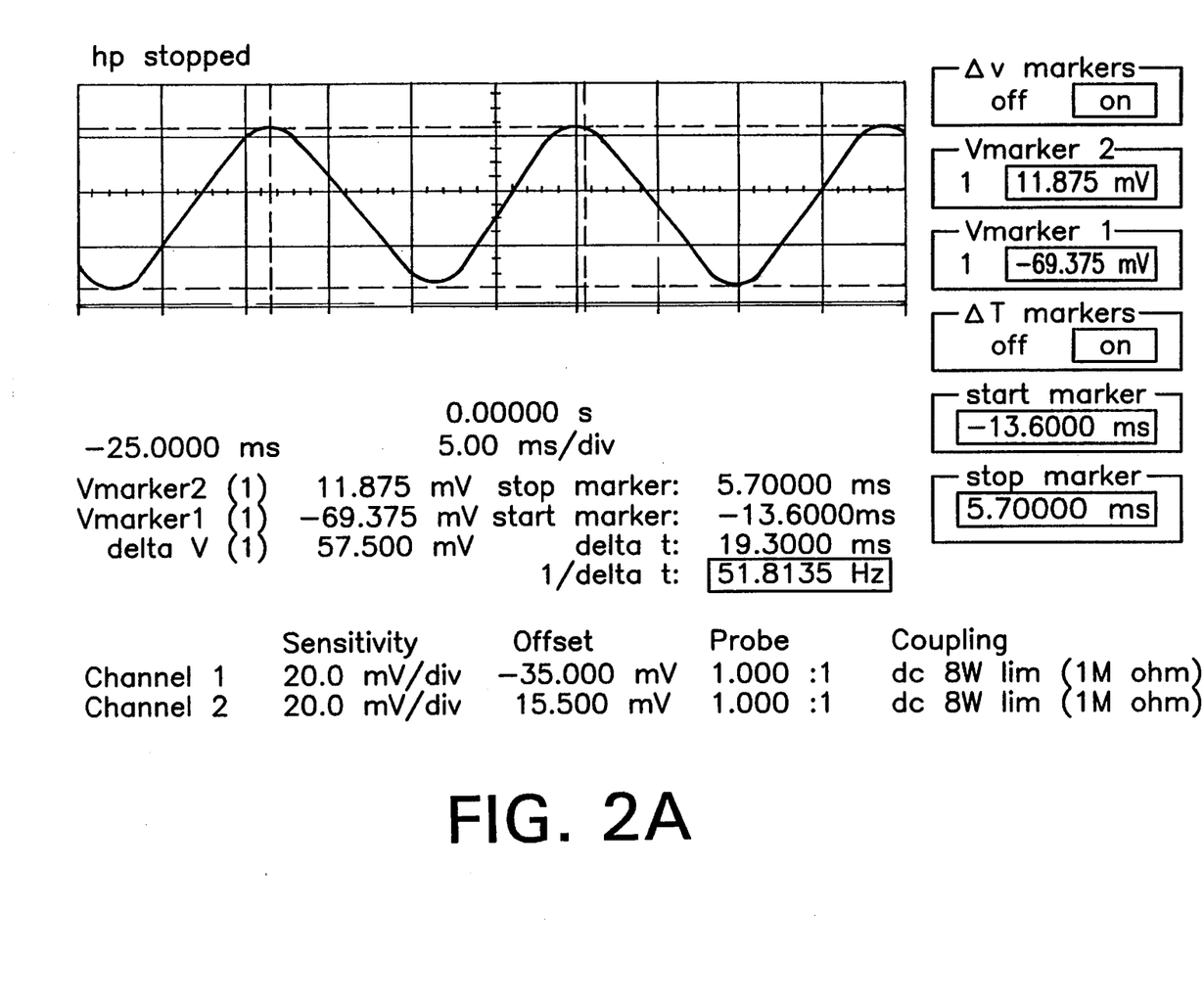
FIGS. 2a through 2c illustrate pressure waveforms which are indicative of the output of the high flow insufflator valve of the present invention operating at various frequencies.
Figure 2B:
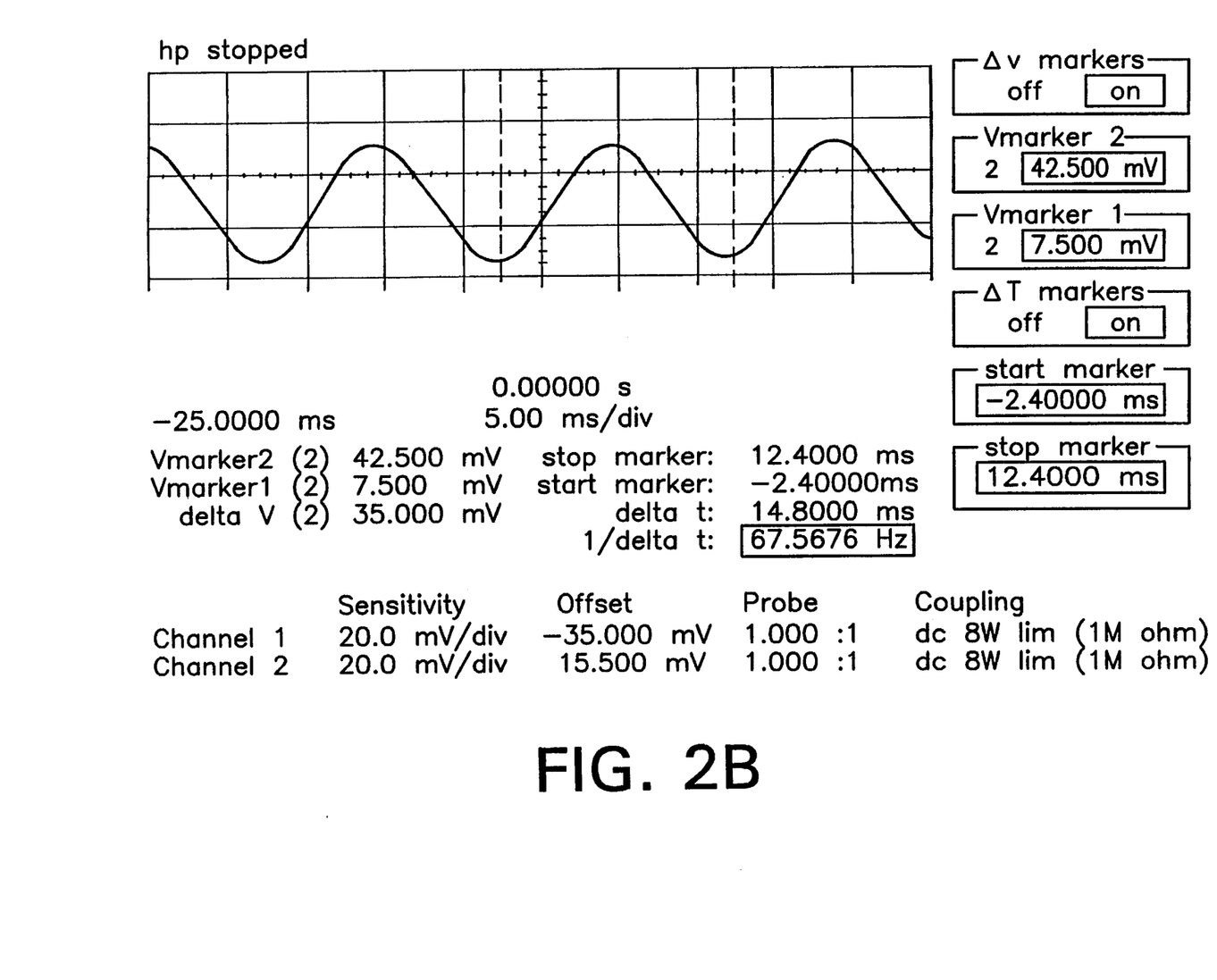
Figure 2C:
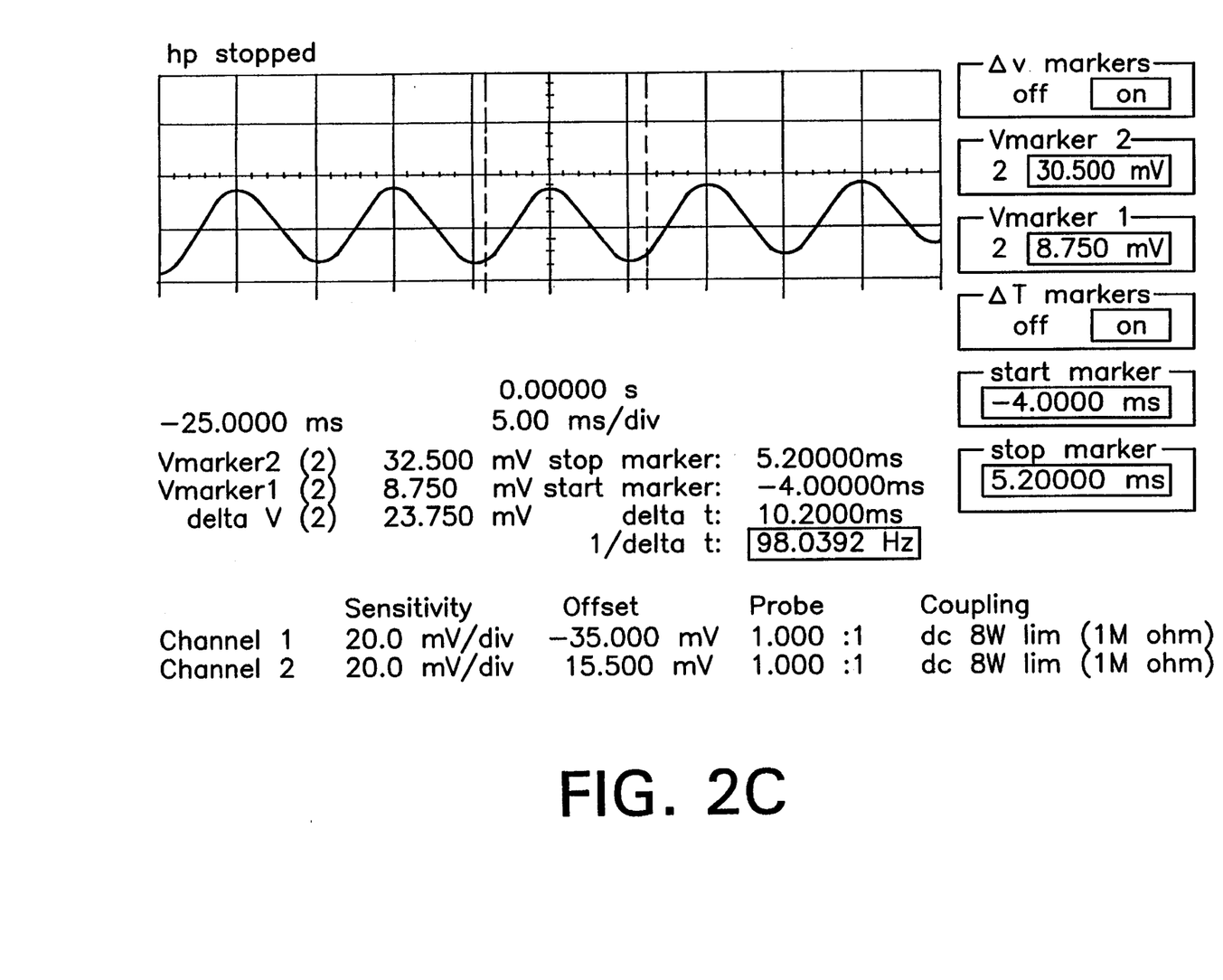

FIGS. 2*a* through 2*c* illustrate the output of the transducer 4 when the DC motor 7 is operated at different frequencies. FIG. 2*a* shows the output of the transducer 4 when the DC motor 7 is operating at about 51.8 Hz. As FIG. 2*a* shows, the amplitude of the waveform at this frequency is relatively high and the area under the waveform is relatively large. FIG. 2*b* shows the output of the transducer 4 when the DC motor 7 is operating at about 68.5 Hz. The amplitude of the waveform at this frequency is less than that at 51.8 Hz. Moreover, the area under the waveform is also less than the area at 51.8 Hz. Lastly, FIG. 2*c* shows the output of the transducer 4 when the DC motor 7 is operating at about 98.0 Hz. The amplitude of the wave form at this frequency is less than the amplitudes at 51.8 Hz and 68.5 Hz. Furthermore, the area under the waveform at this frequency is also less than the areas at 51.8 Hz and 68.5 Hz.

As can be derived from FIGS. 2*a* through 2*c*, the pressure measured by the transducer 4 decreases as the rotational frequency of the perforated disk increases. The pressure measured by the transducer 4 is indicative of the pressure inside the cavity to which the insufflation tube 14 is connected. The measured pressure is also indicative of the flow rate. At lower frequencies, there is time for pressure to build-up in the cylindrical chamber which 2 is evidenced by the larger amplitudes of the measurements from the pressure transducer 4. This, in turn, increases the flow rate. At higher frequencies, the pressure in the cylindrical chamber 2 has less time to build-up which is evidenced by the smaller amplitude of the measurements from the pressure transducer. This, in turn, leads to a decreased flow rate. Accordingly, the inter-cavity pressure can be predicted based on the measurement from the transducer 4 and can be varied by varying the frequency of the DC motor 7. Since the frequency of the DC motor can be almost continuously varied by varying an input voltage or current, the inter-cavity pressure can be continuously controlled by adjusting the voltage or current. Thus, the present invention meets each of its goals. That is, the present invention provides a valve which has a nearly infinitely adjustable displacement volume and which permits an intra-abdominal cavity pressure to be predicted in real time.

What is claimed is:

1. A valve comprising:
   a) an inlet for receiving fluid flow from a fluid source;
   b) a chamber fluidly coupled with the inlet;
   c) a chamber outlet fluidly coupled to the chamber;
   d) a perforated disk having at least one perforation;
   e) an outlet;
   f) a dynamic seal, the dynamic seal having a dynamic seal inlet fluidly coupled with the chamber outlet, and a dynamic seal outlet fluidly coupled with the outlet, and arranged about the perforated disk such that, when the at least one perforation of the perforated disk is aligned with the dynamic seal inlet and the dynamic seal outlet, the dynamic seal inlet is fluidly coupled to the dynamic seal outlet;
   g) a controllable device for rotating the perforated disc; and
   h) a pressure sensor for sensing the pressure in the chamber.

2. The valve of claim 1 wherein the inlet receives fluid flow from a fluid source at a constant pressure.

3. The valve of claim 1 wherein the chamber is cylindrical.

4. The valve of claim 1 wherein the outlet is fluidly coupled with the cavity of a body, whereby a measurement from the pressure sensor is indicative of pressure within the body cavity.

5. The valve of claim 1 wherein the at least one perforation of the perforated disk includes a plurality of equally spaced perforations at a fixed radial distance from a center of the disk.

6. The valve of claim 5 wherein the plurality of perforations are round shaped holes.

7. The valve of claim 5 wherein the plurality of perforations are rectangular shaped holes.

8. The valve of claim 7 wherein the rectangular shaped holes are square.

9. The valve of claim 7 wherein the rectangular shaped holes are slots.

10. The valve of claim 1 wherein the controllable device is a variable frequency motor.

11. The valve of claim 1 wherein the controllable device is continuously adjustable.

12. The valve of claim 1 wherein the perforated disk includes an upstream side and a downstream side, and
   wherein the dynamic seal includes a first part which includes the inlet of the dynamic seal and an outlet fluidly coupled with the inlet of the dynamic seal and located adjacent to the upstream side of the perforated disk, and a second part which includes the outlet of the dynamic seal and an inlet fluidly coupled with the outlet of the dynamic seal and located adjacent to the downstream side of the perforated disk, the first part and the second part being attached.

13. The valve of claim 12 wherein the outlet of the first part includes a concentric step into which is fitted a first top-hat-shaped insert, the first insert containing a fluid pathway fluidly coupled with the outlet of the first part and being biased toward the upstream side of the perforated disk, and wherein the inlet of the second part includes a concentric step into which is fitted a second top-hat-shaped insert, the second insert containing a fluid pathway fluidly coupled with the inlet of the second part and being biased toward the downstream side of the perforated disk.

14. The valve of claim 13 wherein the first part and the second part are brass.

15. The valve of claim 13 wherein the first insert and the second insert are glass.

16. The Valve of claim 13 further including a first doughnut shaped part for biasing the first insert towards the upstream side of the perforated disk and a second doughnut shaped part for biasing the second insert towards the downstream side of the perforated disk.

17. The valve of claim 16 wherein the first doughnut shaped part and the second doughnut shaped part each includes a teflon encased spring.

* * * * *

UNITED STATES PATENT AND TRADEMARK OFFICE
CERTIFICATE OF CORRECTION

PATENT NO. : 5,586,974

DATED : December 24, 1996

INVENTOR(S) : Marcus J. MARTINEZ, et al.

It is certified that error appears in the above-indentified patent and that said Letters Patent is hereby corrected as shown below:

Column 8, line 5, change "Valve" to --valve--.

Signed and Sealed this

Tenth Day of June, 1997

Attest:

BRUCE LEHMAN

Attesting Officer

Commissioner of Patents and Trademarks